United States Patent [19]

Ferrari et al.

[11] Patent Number: 5,214,180

[45] Date of Patent: May 25, 1993

[54] HIGHLY PURE PHOSPHATIDYLINOSITOL OF NATURAL SOURCE USEFUL FOR THE TREATMENT OF CENTRAL NERVOUS SYSTEM DISORDERS AND PROCESS FOR ITS PREPARATION

[75] Inventors: Enrico Ferrari, Sesto San Giovanni; Pier Giuseppe Pagella, Isola S. Antonio; Stefano Maiorana, Milan; Mario Brufani, Castelgandolfo, all of Italy

[73] Assignee: Mediolanum Farmaceutici S.p.A., Milan, Italy

[21] Appl. No.: 821,088

[22] Filed: Jan. 16, 1992

[30] Foreign Application Priority Data

Jun. 7, 1991 [IT] Italy ............... MI91 A 001578

[51] Int. Cl.⁵ .................... C07C 35/16; C07F 9/02
[52] U.S. Cl. ........................ 558/146; 568/15; 568/833
[58] Field of Search .............. 568/15, 833; 558/146

[56] References Cited

U.S. PATENT DOCUMENTS 4,482,761  11/1984  Chao et al. ............... 568/833
4,988,682   1/1991  Kozikowski .............. 568/833

OTHER PUBLICATIONS

Protective Groups in Organic Synthesis; T. W. Greene; 1981; pp. 1, 10–14, 27–28 & 39–50.

Primary Examiner—Marianne M. Cintins
Assistant Examiner—Michael B. Hydorn
Attorney, Agent, or Firm—Oliff & Berridge

[57] ABSTRACT

Phosphatidylinositol of high purity useful for the treatment of central nervous system disorders, prepared from vegetal substances containing it by treating them with reagents suitable for the functionalization of the inositol hydroxy group with protective groups, separating the thus protected phosphatidylinositol by solvent extraction or chromatography, and finally removing said protective groups under conditions which do not modify the phosphatidyl group.

7 Claims, 7 Drawing Sheets

HIGHLY PURE PHOSPHATIDYLINOSITOL OF NATURAL SOURCE USEFUL FOR THE TREATMENT OF CENTRAL NERVOUS SYSTEM DISORDERS AND PROCESS FOR ITS PREPARATION

PRIOR ART

Pure phosphatidylinositol has been obtained up to now by combining various techniques, comprising solvent extraction and repeated purification processes through silica gel-alumina-, and ion exchange resins (Diethylaminoethyl cellulose etc.) chromatographic columns.

Said operations require long separation times and the use of complex solvent mixtures which do not allow to carry out the purification on a commercial scale.

Other techniques (see Japan Patent Application 63-33389) comprise the separation of phosphatidylinositol from complex phosphatid mixtures employing ion exchange resins such as diethylaminoethylcellulose, diethylaminoethylsepharose, QAE Sephadex, in which the phosphatidylinositol was absorbed. This was followed by percolation through the column of a solvent or solvent mixture containing a saline buffer having a higher affinity for the anion exchanger than for phosphatidylinositol.

This technique had two disadvantages: first, it required a very large amount of resins for purifying small amounts of the product and second, it had a very limited separation power.

Other processes for the preparation of phosphatidylinositol are known, starting from yeast which is autolized in toluene and successive extraction of the phospholipids with the aid of a chloroform-methanol mixture.

This process employs a large amount of organic solvents and leads to very low yields of the desired product. The European patent EP 0288569 discloses the preparation of phosphatidylinositol starting from biological substances and comprises its homogeneization in an aqueous saline solution, followed by a series of separation steps by centrifugation, ultra-centrifugation and the use of alkaline or neutral proteases or of gel-chromatography.

This process has the disadvantage of starting from biological products having very low phosphatidylinositol contents thus leading to very small product yields.

Other known methods are:

Preparation of a mixed acid such as 1,2-diacyl-3-glycerophosphatidylinositol starting from crude materials of animal or vegetal origin or from microorganisms (Japanese Patent Application 63-157993).

Purification of phospholipids by using lipases, obtaining a 60 to 70% pure product (Published Japanese patent application Kokai 62-48390).

Various synthetic methods are also known, among which the one reported in J. Med. Chem. 33, 641-646 (1990) (SKF).

Obtaining pure phosphatidylinositol by such methods involves, however, very many steps, while low yields are obtained, and in many cases it is necessary to resolve the racemic compound to obtain the desired product.

For these reasons, the product is scarely suitable for commercial application.

On the other hand it is known that in the therapy of central nervous system disorders such as depressive disorders, tricyclic antidepressive drugs are widely employed, particularly Imipramine (L. S. Goodman & A. Gilman-The Pharmacological Basis of Therapeutics—3rd ed. p. 198-204).

These drugs have a strong antidepressive activity; however, they present serious drawbacks such as a high toxicity, a number of counterindications as well as undesired side effects.

They interfere, for example, with many other drugs such as, for instance, MAOI (monoaminooxidase inhibitors), oral anticoagulants, analgesics, vasodilators; their use in the aftermath of cardiac infarct is advised against; may produce hypo- as well as hypertension, tachycardia, palpitation, arhythmia, confusion state, lack of co-ordination, tremors and several other neurological, hematological, gastroenteric and endocrine disorders. The need is thus felt of drugs which may be more reliable in as far as undesirable side effects are concerned.

SUMMARY

We now have found a process for preparing phosphatidylinositol, which presents, with respect to previously known methods, the advantage of leading to the production of commercial amounts starting from low cost natural products (soya lecithin) through a limited number of simple steps and employing common reagents and solvents, which last can be recovered.

The process for preparing phosphatidylinositol according to the present invention is characterised by:

a) treatment of a vegetal crude material containing at least 10% by wt phosphatidylinositol with reagents suitable to functionalize the inositol hydroxy groups with protective groups;

b) separation of the thus functionalized phosphatidylinositol from the reaction mixture by solvent extraction or chromatography on silica gel;

c) removal of the hydroxyl protective groups in conditions under which the phosphatidyl group is not altered.

The product thus obtained has a phosphatidylinositol content of over 98% and is effective in the treatment of central nervous system disturbance and in particular of memory and depressive ones.

DETAILED DESCRIPTION OF THE INVENTION

The characteristics of the process for preparing phosphatidylinositol of high purity according to the present invention, as well as the chemical and pharmacological characteristics of the product will now be further illustrated in the following detailed description.

The starting material employed in the process according to the present invention, which in what follows will be indicated also as "crude phosphatidylinositol", is a vegetal substance consisting of commercial soya lecithin or, preferably, of a product enriched in phosphatidylinositol to a content of at least 50% and preferably between 50 and 60% by weight.

The product has the following composition:

| | |
|---|---|
| Phosphatidylinositol | 50-60% by wt |
| Phosphatidic acid | 30-40% by wt |
| Phosphatidyl ethanolamine | 0-5% by wt |

Said product is obtained starting from commercial soya lecithin containing 12-13% phosphatidylinositol or from previously enriched soya lecithin containing about 30% phosphatidylinositol and no phosphatidylcholine.

This crude material is brought to a phosphatidylinositol content of 50–60% through the following steps:
- a first treatment with methyl iodide in methanol, benzene or toluene in the presence of sodium- or potassium bicarbonate or carbonate, possibly in the presence of crown ethers (18-crown-6) at room temperature and in a nitrogen atmosphere, by which, the phosphatidylethanolamine contained in the crude material is transformed into phosphatidylcholine;
- phosphatidylcholine is removed from the reaction mixture by extraction with solvents such as 95% ethanol, absolute ethanol, methanol or ethyl acetate;
- successive washing, dehydration and concentration steps, to obtain a crude product containing 50–60% phosphatidylinositol, the rest being as indicated supra.

A further method for obtaining crude phosphatidylinositol consists in reacting enriched soya lecithin (with a phosphatidylinositol content of about 30%) with N-carbethoxyphtalimide in chloroform in the presence of potassium bicarbonate, at room temperature and in nitrogen atmosphere. By this treatment, the phosphatidylethanolamine contained in the crude material is transformed in phtaloyl-phosphatidylethanolamine.

By successive washing with ethyl alcohol, or with ethyl alcoholacetone mixtures, said product is eliminated from the mixture, and a crude having 50–60% phosphatidylinositol is obtained.

In the process for preparing high pure phosphatidylinositol according to the present invention, the crude product, or possibly soya lecithin itself, is first treated with chemical agents to functionalize inositol with groups protecting the hydroxy groups according to the following reaction:

The protective groups must be such as to be removable at the end under mild conditions so as to leave the phosphatidyl groups unchanged.

We have found that compounds suitable to this end are e.g. dimethyltertbutylsilylchloride, thexyldimethylsylilchloride, triemethylsilylchloride and allyl bromide.

The reaction takes place in an organic solvent, at room temperature, in nitrogen.

As solvents, anhydrous pyridine, acetonitrile, DMF and DMSO can be employed.

The thus functionalized phosphatidylinositol is separated from the reaction mixture by solvent extraction employing acetone or a ethyl alcohol-acetone mixture or by rapid filtration on silica gel, employing a $CHCl_3$—$CH_3OH$ from 80:20 to 90:10 mixture, or a ethyl ether hexane 50:50 mixture.

The thus obtained functionalized phosphatidylinositol is then treated to remove the protective groups and to restore the hydroxyinositol groups without modifying the phosphatidyl groups.

This treatment may be obtained by using tetrabutylammonium fluoride in tetrahydrofuran at room temperature, or by basic or acidic hydrolysis at room temperature, or by employing a palladium 10% on carbon catalyst in boiling ethyl alcohol.

The product obtained according to the present invention has a phosphatidylinositol content higher than 98% and is suitable for treating memory and depressive disorders, as demonstrated by the following pharmacological tests.

Pharmacological Tests

By employing the compound obtained as described in example 1, which was indicated as MF-414, studies were performed for determining the effects on the memory and depressive disorders.

As regards the memory disorders the tests were performed on male Wistar (Charles River, Calco) rats of 300–350 g weight. The animals were kept at a temperature of 22° C. with a day/night cycle of 12 hours between 8 and 20 h.

1. Passive avoidance test

The passive avoidance test was performed in a cage divided into two compartments. Training was performed placing the animal on a Plexiglas 5×10 cm platform. The time the animal remains on the platform before descending to the floor grating, where it receives a unavoidable shock (0.8 mA for 2 sec.) is measured.

After 24 hours the animal undergoes the test again and the retention time is measured. The cut off time is of 120 sec. in the training stage, while the retention time is of 300 sec.

The statistical evaluation of the results was performed employing the Mann-Whitney U test.

The results of this series of experiments prove that the compound MF-414, at the dose of 100 mg/kg per os, administered 3 hours before the training test, significantly influences the amnesic effect induced by scopolamine (0.75 mg/kg administered s.c. 30 minutes prior to the training test) in a passive avoidance situation. In particular, the avoidance latency in the group treated with scopolamine +MF-414 was significantly higher than in the group treated with scopolamine only.

Figure 1:
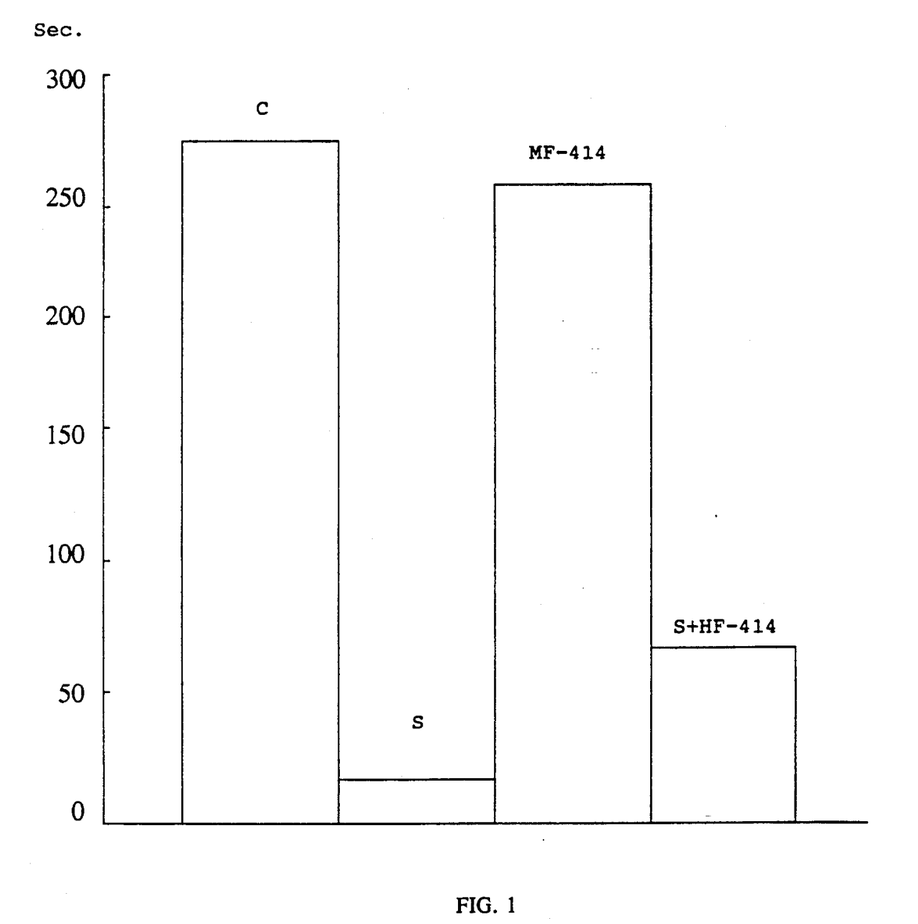

The results are reported in FIG. 1, in which the latency avoidance in sec. for the control group (C), the scopolamine treated group (S) and the one treated with scopolamine plus MF-414 (S+MF-414) ($p<0.05$ vs scopolamine) are illustrated.

2. Spectral Analysis of the EEG frequencies

Apparatus: Brain Surveyor-BASIS TRADE.

On each rat, 6 electrodes with bi-hemispheric electrocortical assembling in frontal and parietal cortex, with central reference electrode and occipital grounding were implanted by means of a stereotazic apparatus.

The implantation was performed under narcosis with Chloropent (3 ml/kg i.p.).

After 72 hours from the implantation, each rat was submitted to EEG monitoring.

Each rat, representing the control of itself, was submitted to a double EEG check performed on two consecutive days and during the same day period (between 14:00 and 17:00). The period of adaptation to the insonorized registration environment and to at constant temperature was of 3 hours (between 11.00 and 14.00).

The EEG signal was analyzed by Fast Fourier Transform (FFT) for a frequency range between 0 and 31 Hz subdivided in the following 6 bands:

Delta: 1-3 Hz
Theta: 3-7 Hz
Alpha: 7-13 Hz (Slow alpha: 7-9 Hz; Fast alpha: 9-13 Hz)
Beta: 13-31 Hz (Slow beta: 13-21 Hz; Fast Beta: 21-31 Hz).

The time of signal analysis was placed at 8 sec. with a time constant at 0.3 sec., LF:0.53 Hz, HF: 50 Hz.

Each spectral energy value was then analyzed and quantified in absolute value (uV2), dominant frequency, absolute energy of each band (uV2), energy percentage of each band on total energy, dominant frequency for each band and brain mapping.

Time scannings were taken every hour on line for 15 min.

The EEG registration was started 3 hrs after per os administration of 100 mg/kg of MF-414) (administration at 11.00, registration at 14.00).

The data obtained were then analyzed by EEG frequency band, as a function of the treatment and of times, by two way variance analysis for measures repeated on one factor.

Figure 2:
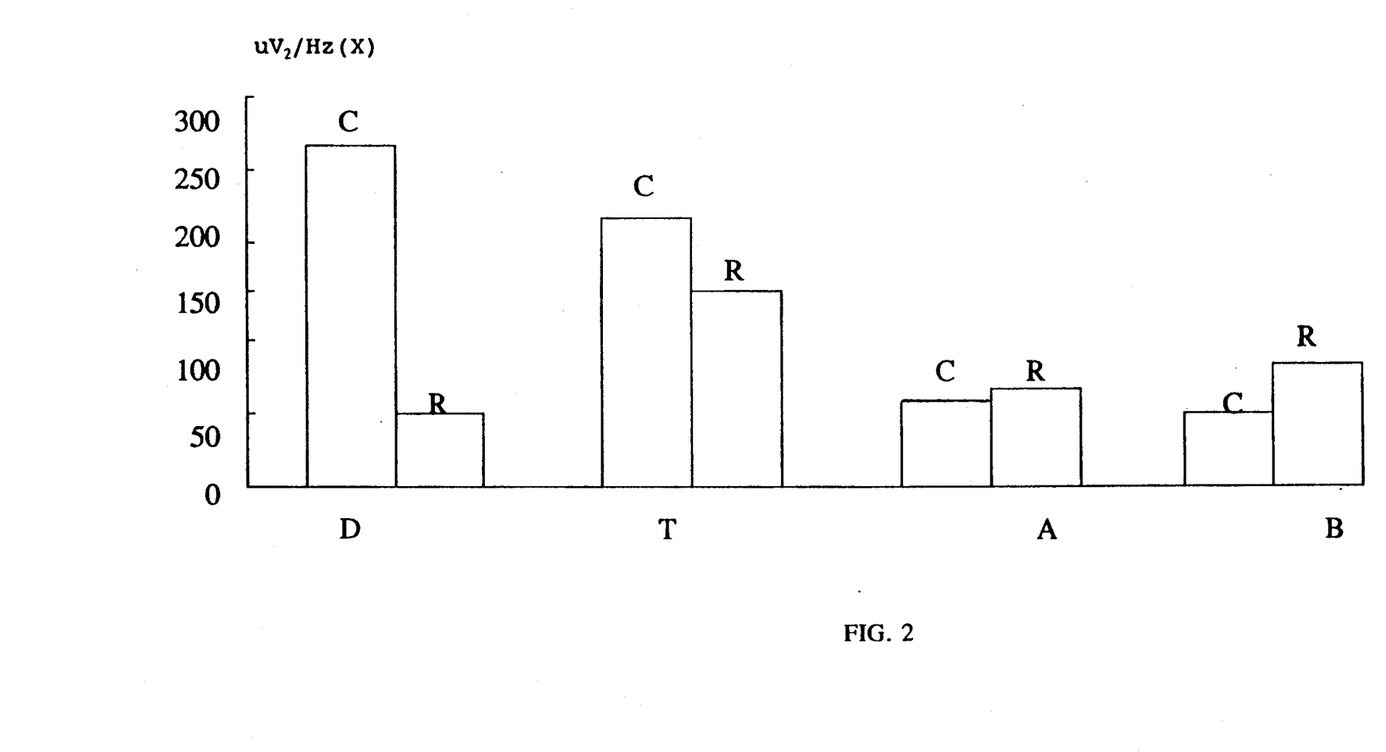

FIG. 2 shows the EEG-CSA (00.50-32.00 Hz). C indicates the control data and R the data referring to the MF-414 treatment (100 mg/kg).

The evaluation of the MF-414 effects on the EEG frequency range between 0 and 31 Hz in the period of time between the fourth and the sixth hour after the administration, shows, as evidenced in FIG. 2, a significative decrease of the slow rhythms (delta) indicated by D, and a slight tendency to an increase of the rapid (beta) frequencies indicated by B.

These tests show that the administration of phosphatydilinositol to adult rats has a protective effect against pharmacologically induced memory alterations. In particular the single administration of phosphatidylinositol antagonizes the amnesic scopolamine effect in a passive avoidance test. Such an effect may be interpreted as an improvement in the memory consolidation processes brought about by the highly pure phosphatidylinositol claimed in the present patent application.

In the alterations of the mnemonic functions many neurotransmitters and neuromodulators are involved. The above results, are interesting in the light of the known correlation existing between memory disorders and a pathologic decrease of the cholinergic function, at least in aged people (scopolamine does in fact mimic said deficiency); however, they do not certify that phosphatidylinositol exerts its pharmacological activity exclusively through a cholinergic mechanism. Other neuromediators, different from acetylcholine, could be involved.

As regards the depressive disorders, the so-called "despair test" (S. Nomura et al., Europ J. Pharmacol. 83 (1982) 171-175) was employed. It is one of the most widely employed screening tests for the evaluation of the antidepressive activity of a drug.

For comparison, Imipramine, a known drug employed for a long time in the therapy of depressive states, was employed. Diazepam, a well known anxiolytic, was also employed for the same purpose.

The test was performed on completely random treatment groups but not in blind. In all cases the pharmacological response was measured by means of an instrument and therefore not influenced by the operator. For the experiments, male CD-1 (ICR-BR) Charles River rats, of average weight at the arrival of 20-22 g, were employed and the experimentation comprised two types, namely single and repeated treatment.

The rat groups for the experiments were:
Group for single treatment with MF-414
Group for repeated treatment with MF-414
Group for single treatment with Imipramin
Group for repeated treatment with Imipramin
Group for single treatment with Diazepam
Group for repeated treatment with Diazepam
Group for single treatment with Placebo
Group for repeated treatment with Placebo
Control groups.

Each cage contained an animal for each treatment group and the administration was done by gastric tube as follows:

a) for single treatment, the administration was performed two hours before the test;
b) for repeated treatment, the administration was performed twice a day, at 9 and 17 hours, for 15 days, with the exception of Saturdays and Sundays when the treatment was done only once, at 9. Because of this sole week-end treatment, no test was performed on Mondays, but only in the successive days.

The drug were administered employing as a vehicle 0.2% methylcellulose, while the Placebo group animals were treated with 0.2% methylcellulose, and the control animals received no treatment. The HCl Imiprimine doses were of 60 mg/kg for the single treatment and of 10 mg/kg twice a day for 15 days, with the above mentioned exception, for the repeated treatment.

The phosphatidyl inositol doses (MF-414) were of 400 mg/kg for the single treatment and of 50 and 100 mg/kg twice a day for 15 days, with the above-mentioned exception for the repeated treatment.

The mentioned MF-414 doses were calculated taking into consideration the percentage of phosphor determined by thin layer chromatography and correcting to 100% for pure product.

Figure 7:
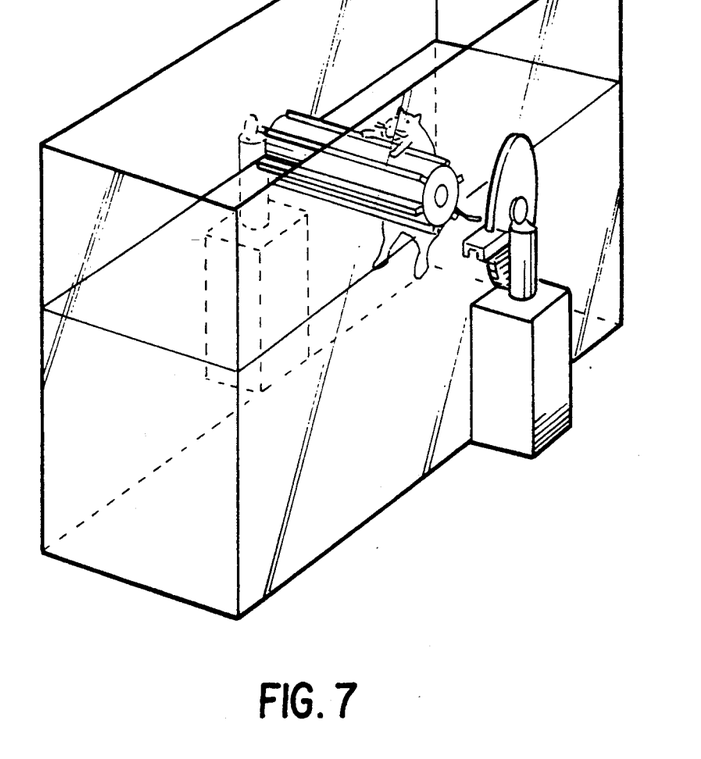

The apparatus employed in the test consisted of a plexiglas container of $10 \times 20 \times 18$ cm as shown in FIG. 7. Inside said container a rotatable paddle-cylinder is mounted in central position. The container is filled with water up to the upper level of the cylinder and the rat is immersed in the water, which has a temperature of 26°-28° C.

The duration of the test for each animal is of 6 minutes. According to the Authors, this period should be divided into two periods of 3 minutes each, in the first of which, from 0 to 3 minutes, the animal, immersed in the water, desperately tries to escape, trying to climb on the paddles, which, however, are rotating and do not let the rat out of the water; in the second period, from 3 to 6 minutes, a depressive state supervenes in the animal because he feels that his attempts to get out are hopeless and desists from his attempts to climb on the cylinder. The activity of the administered product is shown in the escaping attempts during the second period as it antagonizes the depressive state of the animal, resulting from the impossibility of escaping. The registered parameters is the number of turns of the cylinder in each 3 minutes period. The statistical analysis is done inside each period comparing the number of turns of each treatment and quantifying the differences by a crossed comparison according to the Tukey test.

The experiment results are reported in tables 1 to 4 and FIGS. 3 to 6.

Figure 3:
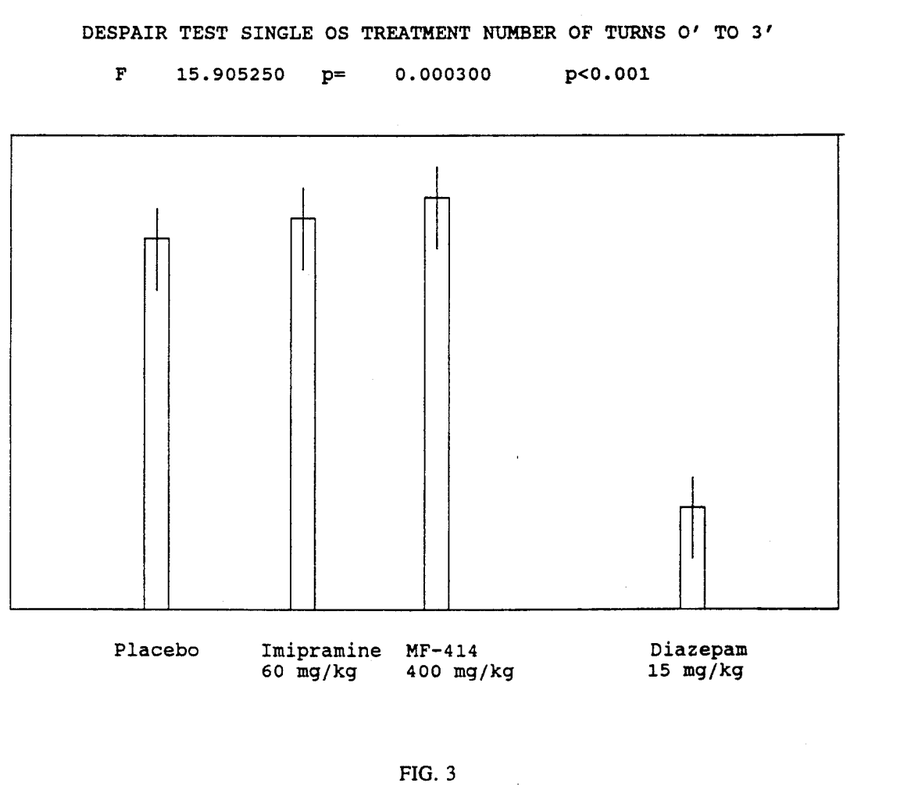

Table 1 and FIG. 3 report the number of turns of the cylinder in the first period (0'-3'), for the single treatment. The product was administered two hours before the test. Table 2 and FIG. 4 report the number of cylinder turns in the second period (3'-6'), also for the single treatment.

As said, the statistical analysis was performed employing the multiple decomposition according to Tukey test, which comprises a crossed comparison among all the groups. In the table headings, the group of reference is indicated employed as comparison. Table 3 and FIG. 5 report the number of turns of the cylinder on the first period (0'-3') of the repeated treatment. The test is performed two hours after the first administration of the fifteenth day of treatment.

Figure 6:
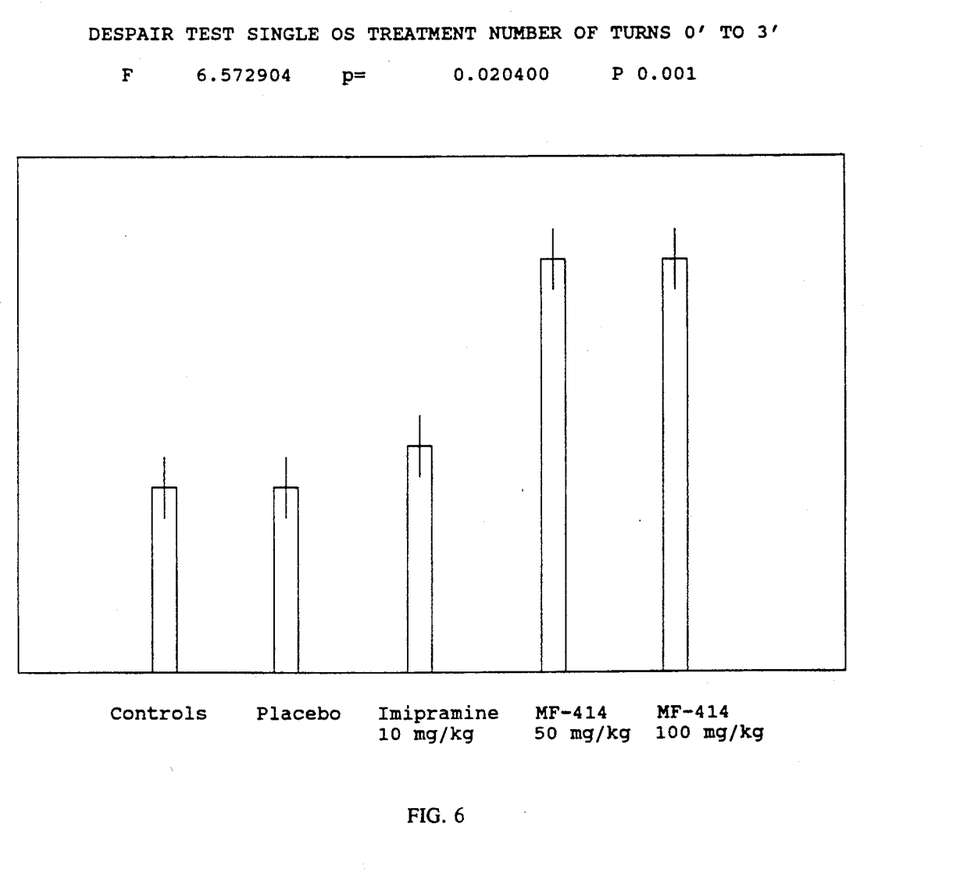

Finally, table 4 and FIG. 6 report the number of turns in the second period (3'-6') of the repeated treatment. Also in this table the title indicates the group of reference employed as statistical comparison.

Figure 4:
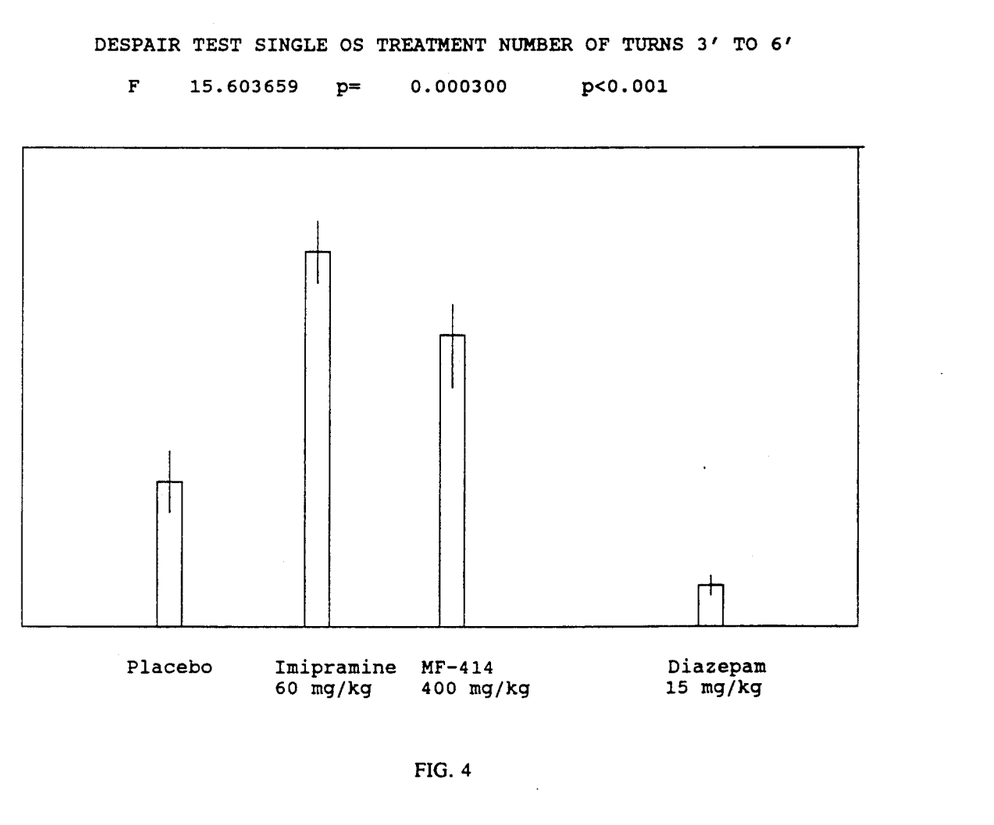
Figure 5:
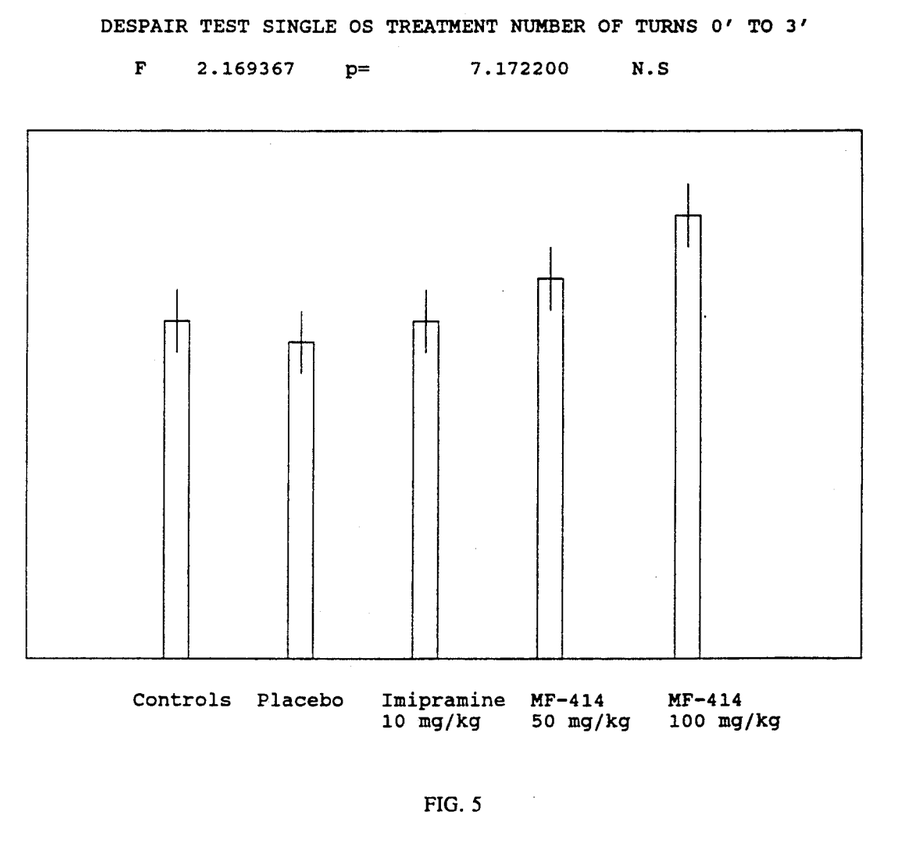

From the tables and figures the following conclusions may be drawn:

a) as to the single treatment, the pharmacologically important result is the one appearing in the second period i.e. the number of turns, from 3' to 6' (table 2 and FIG. 4). Imipramine, a known antidepressant, acts as pharmacologically known, that is it antagonizes the depressive state supervening in the animal when he realizes that it cannot escape. In fact, in this period, the number of turns of the cylinder increases in a statistically significant way vis-a-vis the controls. Phosphatidylinositol (MF-414) also exerts a behavioural effect comparable to the one of Imipramine; in fact, also for the group treated with this compound one observes a statistically significant increase in the number of turns.

The MF-414 dose employed may appear high; however one should take into consideration the fact that, in a mortality test performed in our laboratories, the Imipramine treatment with 300 mg/kg per os causes the death of 5 on 10 animals treated, while a 3000 mg/kg dose per os of phosphatidylinositol has no lethal effect on the 10 animals treated.

Diazepam, as an anxiolytic, also leads to a high decrease in the number of turns both in the first and in the second period. This is in relation with the fact, observed also by the authors of the method, that the animals treated with an anxiolytic do not have the urge to escape and therefore swim quietly in the water.

b) as for the repeated treatment, also in this case the important results are obtained in the second period (Table 4 and FIG. 4). As table 4 shows, while Imipramine in the repeated treatment loses its activity, phosphatidylinositol (MF-414) remains active in a statistically significant way vis-a-vis the other treatment groups. This results prove that phosphatidylinositol has a strong stimulating activity of an antidepressive character on the central nervous system, and that this activity persists in a protracted treatment.

TABLE 1

DESPAIR TEST
NUMBER OF TURNS 0' to 3'—SINGLE TREATMENT

| Tested Groups | Dose mg/kg os | Average | +/− ES | Tukey test vs Placebo $P <$ |
|---|---|---|---|---|
| Placebo | 10 ml | 30.7 | 3.06 | |
| Imipramine | 60 | 31.1 | 2.27 | N.S. |
| MF 414 | 400 | 32.7 | 3.25 | N.S. |
| Diazepam | 15 | 8.9 | 1.73 | 0.01 |

TABLE 2

DESPAIR TEST
NUMBER OF TURNS 3' to 6'—SINGLE TREATMENT

| Tested Groups | Dose mg/kg os | Average | +/− ES | Tukey test vs Placebo $P <$ | Turkey test vs imipramine $P <$ | Turkey test vs MF 414 $P <$ |
|---|---|---|---|---|---|---|
| Placebo | 10 ml | 8.6 | 1.26 | | | |
| Imipramine | 60 | 24.0 | 2.65 | 0.01 | | |
| MF 414 | 400 | 17.7 | 2.11 | 0.05 | N.S. | |
| Diazepam | 15 | 3.3 | 0.88 | N.S. | 0.01 | 0.01 |

TABLE 3

DESPAIR TEST
NUMBER OF TURNS 0' to 3'—REPEATED TREATMENT

| Tested Group | Dose mg/kg os | Average | +/− ES | Tukey test vs Placebo $P <$ |
|---|---|---|---|---|
| Controls | — | 37.7 | 2.29 | |
| Placebo | 10 ml | 36.0 | 3.73 | N.S. |
| Imipramine | 10 | 38.0 | 2.52 | N.S. |
| MF 414 | 50 | 41.6 | 3.43 | N.S. |
| MF 414 | 100 | 48.0 | 2.59 | N.S. |

TABLE NO. 4

DESPAIR TEST
NUMBER OF TURNS 3' TO 6'—REPEATED TREATMENT

| Tested Groups | Dose mg/Kg os | Average | +/− ES | TURKEY TEST vs controls $P <$ | TURKEY TEST vs Placebo $P <$ | TUTKEY TEST vs Imipram. $P <$ | TURKEY TEST vs 414/50 mg $P <$ |
|---|---|---|---|---|---|---|---|
| Controls | — | 9.5 | 1.52 | — | — | — | — |
| Placebo | 10 ml | 10.0 | 2.43 | N.S. | — | — | — |
| Imipramine | 10 | 12.2 | 1.68 | N.S. | N.S. | — | — |
| MF 414 | 50 | 21.7 | 2.42 | 0.05 | 0.05 | 0.05 | — |

TABLE NO. 4-continued

DESPAIR TEST
NUMBER OF TURNS 3' TO 6'—REPEATED TREATMENT

| Tested Groups | Dose mg/Kg os | Average | +/− ES | TURKEY TEST vs controls P < | TURKEY TEST vs Placebo P < | TUTKEY TEST vs Impiram. P < | TURKEY TEST vs 414/50 mg P < |
|---|---|---|---|---|---|---|---|
| MF 414 | 100 | 21.7 | 1.73 | 0.05 | 0.05 | 0.05 | N.S. |

It cannot be excluded, furthermore, that other functions of the organism may be modulated by purified phosphatidylinositol and that, therefore, the claimed product may exert further pharmacological effects, for instance on neuropathies related to diabetes. In fact, a myoinositol deficiency in the nerves of rats, experimentally made diabetic, has been known for some time (D. A. Green et al. J.Clin.Invest. 55, 1326 (1975)).

The invention relates therefore also to the use of said product in the therapy of central nervous system disorders and in particular of the memory and depressive ones, and to the pharmaceutical compositions containing the product as an active principle.

The administration takes place at the dose of between 50 and 1000 mg active principle per day.

We now will give some examples for illustrating the process of preparing phosphatidylinositol according to the invention.

EXAMPLE 1

To a suspension of 400 mg crude 50% phosphatidylinositol (0.24 mmols) in 12 ml anhydrous DMF, in a nitrogen atmosphere, 326 mg (4.8 mmols) imidazol and 362 mg (2.4 mmols) dimethyltertbutylsilylchloride (2.4 mmols) are added. The mixture is left under stirring at room temperature for 1 hour. The solution is then poured in 100 ml water and extracted with ethyl ether (4×50 ml). The ether extract is washed with 50 ml water, then with a saturated ammonium chloride solution (2×50 ml), dried on sodium sulphate and concentrated under reduced pressure. The residue is passed through a silica gel chromatographic column and eluted with 80:20 chloroform/methyl alcohol.210 mg phosphatidylinositol silylate are obtained with 70% yield.

The analysis gives:

$^1$H-NMR (300 MH$_z$, CDCl$_3$) δ; 0.1 (m); 0.85 (m); 1.25 (m); 1.55 (m); 2.0 (m); 2.27 (m); 2.75 (m); 5.32 (m).

IR (film): 3380, 1730, 1460 cm$^{-1}$.

MS FAB m/e=1063 disilyl, 1178 trisilyl.

matrix = 3-nitrobenzylalcohol.

100 mg of the silylated product thus obtained (0.08 mmols) are treated with 101 mg (0.32 mmols) Bu$_4$NF in 10 ml THF at room temperature for a few hours until the starting product has disappeared.

Thin layer chromatography CHCl$_3$/MeOH 80:20. The reaction mixture is taken up with ethyl ether and water. After drying on sodium sulphate, the ether solution is concentrated under reduced pressure. 60 mg of a product with a phosphatidylinositol content higher than 98% are obtained, with 80% yield.

$^1$H-NMR (400 MHz, DMSO-d$_6$).

| | |
|---|---|
| 0.9 | (6H, t, C$\underline{H}_3$) |
| 1.25 | (30H, m, (C$\underline{H}_2$)$_n$—CH$_3$) |
| 1.55 | (2H, m, —CH$_2$—C$\underline{H}_2$—(CH$_2$)$_n$—CH$_3$) |
| 2.05 | (4H, m, —C(=O)—(CH$_2$)$_n$—C$\underline{H}_2$—CH=CH— and CH=CH—C$\underline{H}_2$—(CH$_2$)$_n$—CH—) |
| 2.30 | (2H, m, —O—C(=O)—C$\underline{H}_2$—) |
| 2.80 | (2H, m, —CH=CH—C$\underline{H}_2$—CH=CH—) |
| 3.0–3.7 | (6H, m, Inositol) |
| 3.85 and 3.90 | (2H, m, C$\underline{H}_2$—O—P(=O)(OH)—O—) |
| 4.15 and 4.35 | (2H, m, C$\underline{H}_2$—O—C(=O)—) |
| 5.1 | (1H, m, C$\underline{H}$—O—C(=O)—) |
| 5.3 | (2H, m, —C$\underline{H}$=CH—CH$_2$—CH=CH—) |
| 5.4 | (2H, m, —CH=C$\underline{H}$—CH$_2$—CH=C$\underline{H}$—) |

IR (nujol): 3340, 1735 cm$^{-1}$

EXAMPLE 2

To a solution of 400 mg (0.24 mmols) crude phosphatidylinositol (50% content) in 10 ml anhydrous pyridine, in a nitrogen atmosphere, 0.61 ml trimethylsilychloride (4.8 mmols) and 1.21 ml hexamethyldisilazane (5.76 mmols) are added. The mixture is left for 1 hour at room temperature under stirring.

The solvent is then evaporated under reduced pressure and the residue is purified by chromatography on silica gel (eluent: (CHCl$_3$/CH$_3$OH 80:20).

250 mg phosphatidylinositol pentasilylate are obtained with a 87% yield.

The analysis gives:

$^1$H-NMR (200 MH$_z$, CDCl$_3$) δ: 0.1 (s); 0.85 (m); 1.25 (m); 1.55 (m); 2.00 (m); 2.25 (m); 2.70 (m); 3.20 (m); 3.40 (m); 3.52 (m); 5.30 (m).

IR (liquid film): cm$^{-1}$ 3430 (OH), 3000, 2920, 2850 (CH$_2$, CH), 1740 (C=O), 1250 (P=0).

A solution of 200 mg of the silylate product obtained in 30 ml ethyl ether, is treated for 4 hours at room temperature with 20 ml 0.1N HCl.

The ether layer is then separated from the aqueous one, dried on magnesium sulphate and concentrated under reduced pressure. 120 mg product are obtained having a phosphatidylinositol content higher than 99%, with a 86% yield.

$^1$H-NMR (400 MH$_z$, DMSO-d$_6$)

| | |
|---|---|
| 0.9 | (6H, t, C$\underline{H}_3$) |
| 1.25 | (30H, m, (C$\underline{H}_2$)$_n$—CH$_3$) |
| 1.55 | (2H, m, —CH$_2$—C$\underline{H}_2$—(CH$_2$)$_n$—CH$_3$) |
| 2.05 | (4H, m, —C(O)—(CH$_2$)$_n$—C$\underline{H}_2$—CH=CH— and CH=CH—C$\underline{H}_2$—(CH$_2$)$_n$—CH—) |
| 2.30 | (2H, m, —O—C(O)—C$\underline{H}_2$—) |
| 2.80 | (2H, m, —CH=CH—C$\underline{H}_2$—CH=CH—) |
| 3.0–3.7 | (6H, m, Inositol) |
| 3.85 and 3.90 | (2H, m, C$\underline{H}_2$—O—P(OH)—O—) |
| 4.15 and 4.35 | (2H, m, C$\underline{H}_2$—O—C(O)—) |
| 5.1 | (1H, m, CH—O—C(O)—) |
| 5.3 | (2H, m, —C$\underline{H}$=CH—CH$_2$—C$\underline{H}$=CH—) |
| 5.4 | (2H, m, —CH=C$\underline{H}$—CH$_2$—CH=C$\underline{H}$—) |

IR (nujol) 3340, 1735 cm$^{-1}$.

EXAMPLE 3

A solution of 2 g crude (50%) phosphatidylinositol (1.2 mmols), 3.27 g (48 mmol) imidazol, 26 g (24 mmols) trimethylsilylchloride and 4.64 g (28.8 mmols) hexamethyldisilazane in 80 ml anhydrous acetonitrile, is kept under stirring in a nitrogen atmosphere at room temperature for 2 hours.

The mixture is then diluted with 150 ml ethyl ether and washed with water (2×50 ml) and then with a saturated sodium chloride solution (2×50 ml).

The organic layer is then dried on sodium sulphate and concentrated under reduced pressure. The residue is extracted with a 1:1 (v/v) ethyl alcohol/acetone mixture (20 ml). The solution of phosphatidylinositol is concentrated under reduced pressure and the residue is employed in the successive step without any further treatment.

1.07 g pentasilylate derivative are obtained (heavy oil) with a 75% yield.

The analysis gives:

$^1$H-NMR (200 MH$_z$, CDCl$_3$) δ; 0.10 (s); 0.85 (m); 1.25 (m); 1.55 (m); 2.00 (m); 2.25 (m); 2.70 (m); 3.20 (m); 3.40 (m); 3.52 (m); 5.30 (m).

IR (liquid film) cm$^{-1}$ 3430 (OH), 3000, 2920, 2850 (CH$_2$, CH), 1740 (C=O), 1250 (P=O).

To 350 mg (0.293 mmols) of the obtained silylated product in 10 ml THF, 3.2 ml (3.52 mmols) tetrabutylammonium fluoride 1.1M solution in THF are added.

The solution is stirred for 4 hours at room temperature; it is then acidified with 1N HCl and diluted with ethyl ether.

The ether layer is then washed with saturated sodium chloride solution, dried on sodium sulphate and concentrated under reduced pressure.

The residue is suspended for 30 minutes in 10 ml of a ethyl alcohol-acetone mixture. The solid residue consisting of phosphatidylinositol is filtered and dried under 1 mm/Hg pressure at room temperature for 4 hours.

200 mg product with a phosphatidylinositol content higher than 98% are obtained (82% yield). The analysis gave results identical to the ones of the preceding example.

EXAMPLE 4

A suspension of 16 g soya lecithin (phosphatidylinositol content ca. 13%) 6.8 g (0.1 mol) imidazol, 6.3 ml (0.05 mol) trimethylsilylchloride, 12.7 ml (0.06 mol) hexamethyldisilazane in 480 ml anhydrous acetonitrile is stirred for 3 hours at room temperature in a nitrogen atmosphere.

The mixture is then diluted with 600 ml ethyl ether and washed first with water (3×200 ml) and then with a saturated sodium chloride solution (2×200 ml).

The organic layer is dried on sodium sulphate and concentrated under reduced pressure.

The crude product is extracted with a 1:1 v/v ethyl alcohol-acetone mixture.

The solution of silylated phosphatidylinositol is concentrated under reduced pressure and the residue is employed in the successive step without any further treatment.

1.52 g pentasilylated phosphatidylinositol, with a 51% yield, are obtained.

This product is de-silylated as in Example 3. 0.85 g of a product with over 98% phosphatidylinositol are obtained.

EXAMPLE 5

260 mg (11 mmols) sodium metal are dissolved in 15 ml anhydrous DMSO. To the solution, 3.34 g crude 50% phosphatidylinositol (2 mmols) and 2.7 ml (20 mmols) allyl bromide are added.

The mixture is left for 4 hrs under stirring at room temperature until the reaction is completed.

The reaction product is purified by column chromatography employing a 50:50 ethyl ether-hexane mixture as eluent.

1.45 g pentaallylated phosphatidylinositol are obtained with a 70% yield.

The NMR analysis gives:

$^1$H-NMR (90 MH$_z$, CDCl$_3$) δ: 0.85 (m); 1.25 (m); 2.0 (m); 2.75 (m); 5.3–5.6 (m); 5.62–5.90 (m); 6.0–6.4 (m).

To a solution of 1 g (0.96 mmols) of pentaallylated, obtained as described, in 30 ml ethyl alcohol and 1 ml water, 65 mg (0.34 mmols) paratoluenesulphonic acid and 0.8 g palladium (10% on carbon) are added.

The mixture is heated on reflux for a few hours until the allyl groups have disappeared (controlled with an ethyl ether/hexane 50:50 mixture by thin layer chromatography).

The catalyst is filtered off and the solution evaporated under reduced pressure.

The residue is taken up in methylene chloride and the solution is washed with a saturated sodium bicarbonate solution, and then with water, dried on sodium sulphate and concentrated under reduced pressure.

The obtained product is purified by chromatography on silica gel employing a chloroform/methanol eluent.

0.6 g product are obtained, higher than 98% in phosphatidylinositol, with a 75% yield.

The analysis indicates:

$^1$H-NMR (200 MH$_z$, —CDCl$_3$) δ: 0.85 (m); 1.25 (m); 1.55 (m); 2.05 (m); 2.30 (m); 2.75 (m); 5.30 (m).

IR (nujol); 3340, 1735, cm$^{-1}$.

We claim:

1. Process for the preparation of highly pure phosphatidylinositol, suitable for the treatment of central nervous system disorders, comprising:
   a) treating a crude material of vegetal origin, containing at least 10% by weight phosphatidylinositol with reagents which functionalize the inositol hydroxy groups with protective groups, said reagents being selected from the group consisting of dimethyltertbutylsilylchloride, thexyldimethylsilylchloride, trimethylsilylchloride and allyl bromide;
   b) separating the thus functionalized phosphatidylinositol from the reaction mixture by solvent extraction or by chromatography on silica gel; and
   c) removing the protective groups under conditions such as not to modify the phosphatidyl group.

2. Process according to claim 1, wherein the crude material contains 50 to 60% by weight phosphatidylinositol.

3. Process according to claim 1, wherein said treating is performed in an anhydrous organic solvent selected from the group consisting of pyridine, acetonitrile, dimethylformamide and dimethylsulfoxide; at room temperature and in a nitrogen atmosphere.

4. Process according to claim 1, wherein chromatographic separation is performed employing as eluent, a 80:20 to a 90:10 chloroform-methanol mixture, or a 50:50 mixture of ethyl ether and hexane.

5. Process according to claim 1, wherein said removing is performed by treatment with tetrabutylammonium fluoride in tetrahydrofuran at room temperature.

6. Process according to claim 1, wherein said removing is performed by acidic or basic hydrolysis at room temperature.

7. Process according to claim 1, wherein said removing is performed by utilizing a 10% Pd/C catalyst in ethyl alcohol under reflux at boiling temperature.

* * * * *